United States Patent [19]

Chiang et al.

[11] Patent Number: 4,713,391
[45] Date of Patent: Dec. 15, 1987

[54] AZABICYLOALKANE PHENYL SUBSTITUTED ALKANE CARBOXYLATES, THEIR PREPARATION AND USE AS ANTICHOLINERGIC AGENTS

[75] Inventors: Peter K. Chiang, Bethesda; Michelle M. Richard, Silver Spring; Felipe N. Padilla, Wheaton, all of Md.; Frank I. Carroll, Durham; Philip Abraham, Cary, both of N.C.

[73] Assignees: The United States of America as represented by the Secretary of the Army, Washington, D.C.; Research Triangle Institute, Research Triangle, N.C.

[21] Appl. No.: 855,857

[22] Filed: Apr. 17, 1986

[51] Int. Cl.$^4$ .................... C07D 209/02; H61K 31/40
[52] U.S. Cl. ..................... 514/412; 548/452
[58] Field of Search .................. 548/452; 514/412

[56] References Cited

U.S. PATENT DOCUMENTS 4,499,099 2/1985 Watts ........................... 548/452 X
4,533,498 8/1985 Blaney et al. .................. 548/452 X

OTHER PUBLICATIONS

Furstoss et al., Chem. Abstracts, 72, (1970), entry 111268z.
House, *Modern Synthetic Reactions*, W. A. Benjamin, Inc., N.Y., (1965), pp. 54–55.
Kaplan, J. Am. Chem. Soc., 88, (1966), 4970–4971.
Sonntag, Chem. Revs., 52, (1953), 312–399.

*Primary Examiner*—Donald G. Daus
*Assistant Examiner*—William A. Teoli, Jr.
*Attorney, Agent, or Firm*—Francis A. Cooch; Werten F. W. Bellamy

[57] ABSTRACT

This invention relates to novel compositions, their preparation and the use thereof as anticholinergic agents in the treatment or prophylaxis of organophosphate or nerve gas poisoning in animals. These compositions and pharmaceutical preparations containing them in their free base form and acid addition salts thereof are represented by the formula

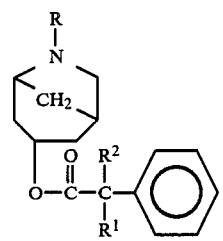

wherein R represents lower alkyl groups containing 1 to 7 carbon atoms; $R^1$ represents hydrogen, phenyl, cyclohexyl, and cyclopentyl; and $R^2$ represents lower alkyl groups containing 1 to 7 carbon atoms, hydroxymethyl, and hydroxyl.

11 Claims, 2 Drawing Figures

AZABICYLOALKANE PHENYL SUBSTITUTED ALKANE CARBOXYLATES, THEIR PREPARATION AND USE AS ANTICHOLINERGIC AGENTS

BACKGROUND OF THE INVENTION

1. Field of the Invention

This invention relates to the preparation and use of azabicycloalkane phenyl substituted alkane carboxylates, including pharmacologically useful compositions thereof, as anticholinergic agents.

2. Prior Disclosure

Nerve gas poisons function by irreversibly inhibiting acetylcholinesterase (AChE). This leads to a build up of excess acetylcholine resulting in overstimulation of both the peripheral and central nervous system. A single acute dose of a nerve gas can lead to death with the primary cause of death being respiratory failure.

The organophosphate nerve agents GD (soman), GB (sarin) and VX are extremely potent cholinesterase inhibitors (anticholesterases). Like other organophosphate poisons, they owe their biological activity to phosphylation of serine hydroxyl at the active site of the enzyme acetylcholinesterase, thereby deactivating it in an essentially irreversible manner. As a consequence of this deactivation, the neurotransmitter acetylcholine accumulates at cholinergic sites, producing an effect roughly equivalent to continuous stimulation of cholinergic fibers throughout the central and peripheral nervous systems.

Standard therapy for organophosphate nerve agent poisoning is based on the concurrent administration of an anticholinergic agent to antagonize the effects of the accumulated acetylcholine and a cholinesterase reactivator to dephosphylate the inhibited enzyme. The standard anticholinergic agent used in therapy is atropine sulfate. Pyridinium oximes such as 2-[(hydroxyimino)methyl]-1-methylpyridinium halide (2-PAM) are the most studied cholinesterase reactivators. Various other drugs have been examined as adjuncts to this therapy in order to control the convulsions which are a side-effect of the poisoning, to assist in countering respiratory failure, or because of their antimuscarinic properties. Specific examples are benactyzine, and aprophen. Atropine is known to antagonize the muscarinic effects of acetylcholine and is the best-known of the so-called antimuscarinic agents. The usefulness of atropine has stimulated the study of other antimuscarinic agents as potential treatment drugs for anticholinesterase poisoning.

Since the ionic nature of many cholinesterase reactivators limits their efficacy to the peripheral nervous system, the anticholinergic drugs are the primary source of protection for the central nervous system. The practical usefulness of the anticholinergic drugs is limited by their central nervous system activities and their toxicities.

There is a need for new effective anticholinergic agents for the pre-treatment (prophylaxis) against and treatment of organophosphate nerve agent poisoning. Like atropine, such agents must exhibit a higher affinity than acetylcholine for the receptor sites. In addition, neutral molecules with some degree of lipid solubility are preferred because of their ability to penetrate the bloodbrain barrier and protect the central nervous system. Benactyzine and aprophen are two examples of such compounds. Compounds which are more effective antimuscarinic agents than atropine, benactyzine, and aprophen are potentially good candidates for therapeutically useful drugs.

PHARMACOLOGICAL INFORMATION

The nature of muscarinic receptors has been studied mainly by investigating the chemical and physical characteristics of the drugs with which they interact. The formation of a drug-receptor complex involves interactions of several different types between groups in the drug molecule and in the receptor. The power of a drug to become attached to a receptor has been termed its affinity while its ability to induce or antagonize a stimulus has been called either intrinsic activity or efficacy.

The activities of muscarinic drugs and their antagonists may be assayed on isolated pieces of gut (usually guinea-pig ileum or rabbit duodenum) suspended in a suitable oxygenated medium. Agonists produce contractions of such preparations which are blocked by pre-treatment with anticholinergic drugs. Several methods normally used for determining the activity of antagonists are based upon that described by Schild in *Brit. J. Phrmacol.*, Vol. 2, page 189 (1947), and the antagonistic activity is usually expressed as a $pA_2$ value, i.e. the negative logarithm of the molar concentration of the antagonist which reduces the effect of a double dose of the agonist to that of a single one. Alternatively, $pA_2$ can be defined as representing the negative logarithm of $K_B$, which is the affinity of a drug to bind a receptor. It is obvious that this assay does not measure precisely and selectively only one type of pharmacological activity. However, when used with an understanding of its scope and limitations, it does provide valuable information in the development of anticholinergic drugs and their structure-activity relationship. Additionally, another method to assay the activity of agonists or antagonists for the muscarinic receptors is their effect on the release of $\alpha$-amylase from isolated pancreatic acini cells as described in *American J. Physiol.*, Volume 235, pages 743–747, (1978); and *J. Physiol.*, Volume 270, pages 439–454, (1977). A prototype agonist, such as carbachol, stimulates the release of $\alpha$-amylase by acting on the muscarinic receptors of pancreatic acini cells. The potency of an antagonist on the muscarinic receptors is measured by its ability to inhibit the release of $\alpha$-amylase stimulated by carbachol. Like the ileum assay, it is a reliable assay for the potencies of muscarinic anticholinergic agents.

SUMMARY OF THE INVENTION

Figure 1:
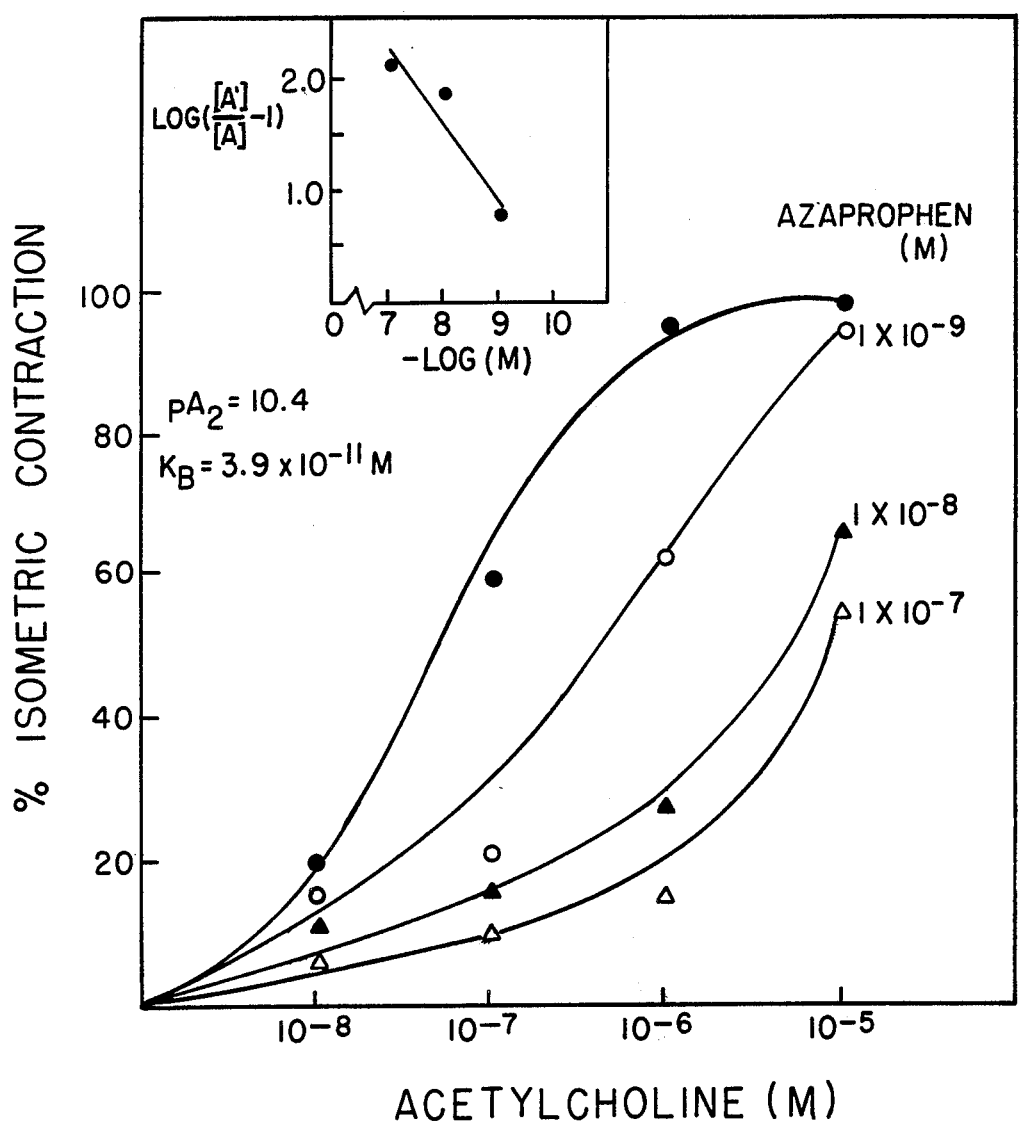
FIG. 1 illustrates the inhibition of the acetylcholine-induced contraction of guinea pig ileum by azaprophen.

This invention relates to novel azabicycloalkane phenyl substituted alkane carboxylate compositions, their preparation and the use thereof as anticholinergic agents in the treatment or prophylaxis of nerve gas poisoning in animals. These compositions and pharmacologically useful preparations containing them in their free base form and acid addition salts thereof are represented by the formula

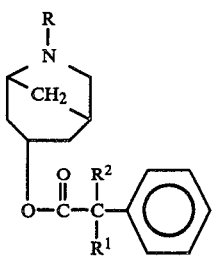

wherein R represents lower alkyl groups containing 1 to 7 carbon atoms; $R^1$ represents hydrogen, phenyl, cyclohexyl, and cyclopentyl; and $R^2$ represents lower alkyl groups containing 1 to 7 carbon atoms, hydroxymethyl, and hydroxyl. These compositions are referred to by applicants as azabicycloalkane phenyl substituted alkane carboxylates which especially includes azaprophen and related compounds.

DETAILED DESCRIPTION OF THE INVENTION

Practical utility has been established for compositions and pharmaceutical preparations containing them in their free base form and acid addition salts thereof are represented by the formula

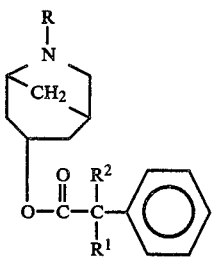

where R represents lower alkyl groups containing 1 to 7 carbon atoms; $R^1$ represents hydrogen, phenyl, cyclohexyl, and cylopentyl; and $R^2$ represents lower alkyl groups containing 1 to 7 carbon atoms, hydroxymethyl, and hydroxyl. The lower alkyl groups include methyl, ethyl, n-propyl, isopropyl, n-butyl, tertiary-butyl, n-pentyl, isopentyl or heptyl, especially methyl, as well as ethyl and propyl.

Salts of compounds of the present invention are acid addition salts, especially pharmaceutically useful non-toxic acid addition salts, such as those with inorganic acids, for example, hydrochloric, hydrobromic, nitric, sulphuric, or phosphoric acid, or with organic acids, such as organic carboxylic acids, for example, acetic, propionic, glycollic, malonic, succinic, maleic, hydroxymaleic, methylmaleic, fumaric, malic, tartaric, citric, benzoic, cinnamic, mandelic, salicylic, 4-aminosalicylic, 2-phenoxybenzoic, 2-acetoxybenzoic, embonic, nicotinic or isonicotinic, or organic sulfonic acids, for example, methanesufonic, ethanesulfonic, 2-hydroxy-ethanesulfonic, ethane-1,2-disulfonic, benzenesulfonic, p-toluene-sulfonic, naphthalene-2-sulfonic, or cyclohexane sulfamic acid, as well as ascorbic acid.

In view of the close relationship between the new compounds in their free form and in the form of their salts, the free compounds or their salts are in this context and whenever appropriate, to be understood as also representing the corresponding salts and free compounds, respectively.

The compositions of this invention are water soluble and can be administered to the animal systemically (i.e. orally or parenterally) either prior to and/or after it has been exposed to organophosphate poisoning. These compositions are obtained by a method which is in itself novel, which comprises the steps of (a) reducing a compound having the formula:

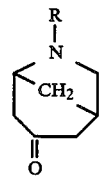

with $LiALH_4$ to form the corresponding derivative

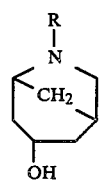

(b) reacting the hydroxyl derivative formed in step (a) with a compound having the formula

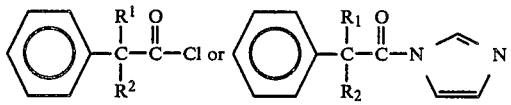

This novel method for the preparation azabicycloalkane phenyl substituted alkane carboxylates is illustrated in the following chemical reaction sequence for the preparation of azaprophen:

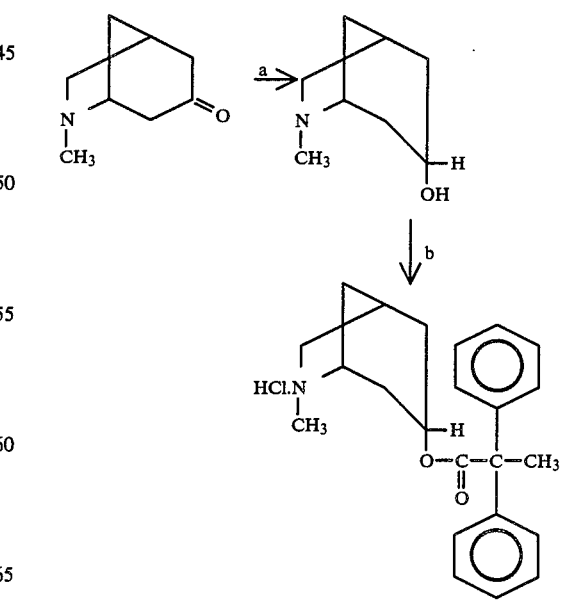

(a) $LiAlH_4$
(b) $(C_6H_5)_2C(CH_3)C(O)Cl$

MATERIALS AND METHODS

Applicants have prepared several compounds as potential anticholinergics and assayed them for antimuscarinic activity. The chemical structural relationship between azaprophen (6-methyl-6-azabicyclo[3.2.1]-octane-3α-ol 2,2-diphenylproprionate) and other anticholinergic agents depicted in the structures below:

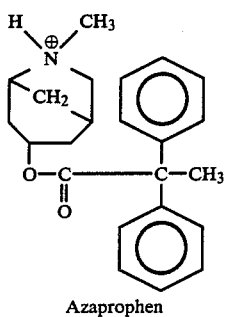

Azaprophen

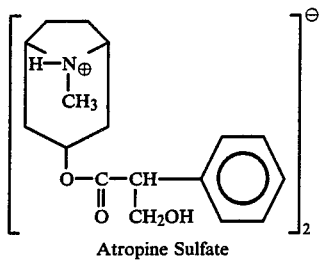

Atropine Sulfate

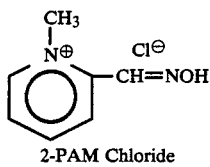

2-PAM Chloride

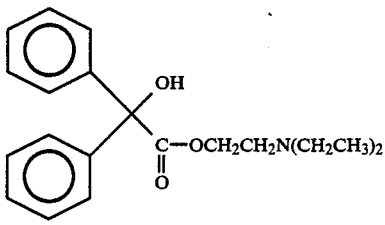

Benactyzine

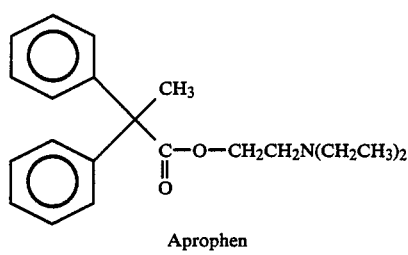

Aprophen

As indicated by the results in the Table below, azaprophen showed much greater anticholinergic activity in the guinea-pig ileum antimuscarinic assay than atropine, benactyzine, and aprophen.

It is well established that activity in the guinea-pig ileum antimuscarinic assay correlates with in vivo anticholinergic activity. All presently used drugs show high activity in this screen. The activity of azaprophen is much greater than compounds presently in use. Azaprophen is a novel anticholinergic drug useful for treatment or prevention of nerve gas poisoning. It should also be useful for treatment of poisoning by organophosphorus insecticides, in ophthalmology to produce a dilatation of the pupil (mydriasis), as bronchial dilators, and before operations to inhibit bronchial secretions and to block the vagus nerve. The treatment of various conditions like colic where contractions of smooth muscle cause intense pain, and the treatment of Parkinson's disease and motion sickness are other potential uses of this drug.

METHODS

Guinea Pig Ileum Assay

The ability of azaprophen to block the acetylcholine-induced contraction of the guinea pig ileum was assayed according to the method of M. C. Pankaskie, et al., *J. Medicinal Chemistry* Vol. 28 pages 1117, (1985); R. K. Gordon and P. K. Chiang, *J. Pharmacology and Experimental Therapeutics*, Vol. 236, pages 85–89 (1986); and "Pharmacological Experiments on Isolated Preparations", Department of Pharmacology, University of Edinburg, pages 58–87, 1970. Distal ileum was obtained from male albino guinea pigs (200–500 grams). A segment of distal ileum about 20 cm in length was excised 5 cm above the ileo-caecal junction and immediately placed in oxygenated Krebs-Ringer solution containing 118 mM NaCl, 4.7 mM KCl, 25 mM $NaHCO_3$, 0.93 mM $KH_2PO_4$, 2.5 mM $CaCl_2$, 1.2 mM $MgCl_2$, and 11 mM glucose. Segments 2.5 cm in length were suspended in a 10 ml organ bath, which was aerated with 5% $CO_2$ and 95% $O_2$, and maintained at 37° C. Isometric contractions were recorded by a transducer (Harvard Apparatus, Natick, MA) at 1 gram tension. The concentration response curve for acetylcholine (ACh) was obtained using a series of ACh doses of increasing concentration; the maximal contractile response was designated 100%. The antimuscarinic activity of azaprophen (ability to block the ACh-induced contraction) was expressed as the $K_B$ or $pA_2$ values, which were calculated using computer programs for the Schild plot as described by R. J. Tallarida, et al., in *Manual of Pharmacological Calculations With Computer Programs*, pages 29–31, (1981).

α-Amylase Release from Pancreatic Acini Cells

Pancreatic acini cells were prepared from a male Sprague Dawley rat (150 grams) according to a modification of the procedures of S. R. Peikin, et al., *American Journal Physiology*, Vol. 235, pages 743 to 747 (1978) which is described by R. K. Gordon and P. K. Chiang, *J. Pharmacology and Experimental Therapeutics*, Vol. 236, pages 85 to 89, (1986). Dispersed pancreatic acini cells were prepared by three successive incubations with collagenase (0.8 mg/ml, Sigma Co.) and resuspended in 16 ml of Dulbecco's minimum essential medium containing 0.2% albumin, 0.01% trypsin inhibitor, and 0.09% theophylline, aerated with 100% $O_2$, and diluted 1:5 before use. Viability test by trypan blue exclusion was greater than 99%. Dispersed acini were incubated with varied doses of azaprophen and $1 \times 10^{-5}$M carbachol in 0.5 ml of incubation medium. α-Amylase secreted from the acini was determined as described by J. D. Gardner, et al., in "Regulation of Amylase Release From Dispersed Pancreatic Acinar Cells", *J. Physiol*, Vol. 270, pages 439–454, (1977) using the Phadebas kit (Pharmacia) diluted 1:2. The $I_{50}$, the concentration of azaprophen required for 50% inhibition was calculated by a computer program ALLFIT, as described by P. J. Munson, et al., in "Computer Modeling of Several Ligands Binding to Multiple Receptors", *Endocrinology*, Vol. 105, pages 1377-1381, (1979).

RESULTS

Figure 2:
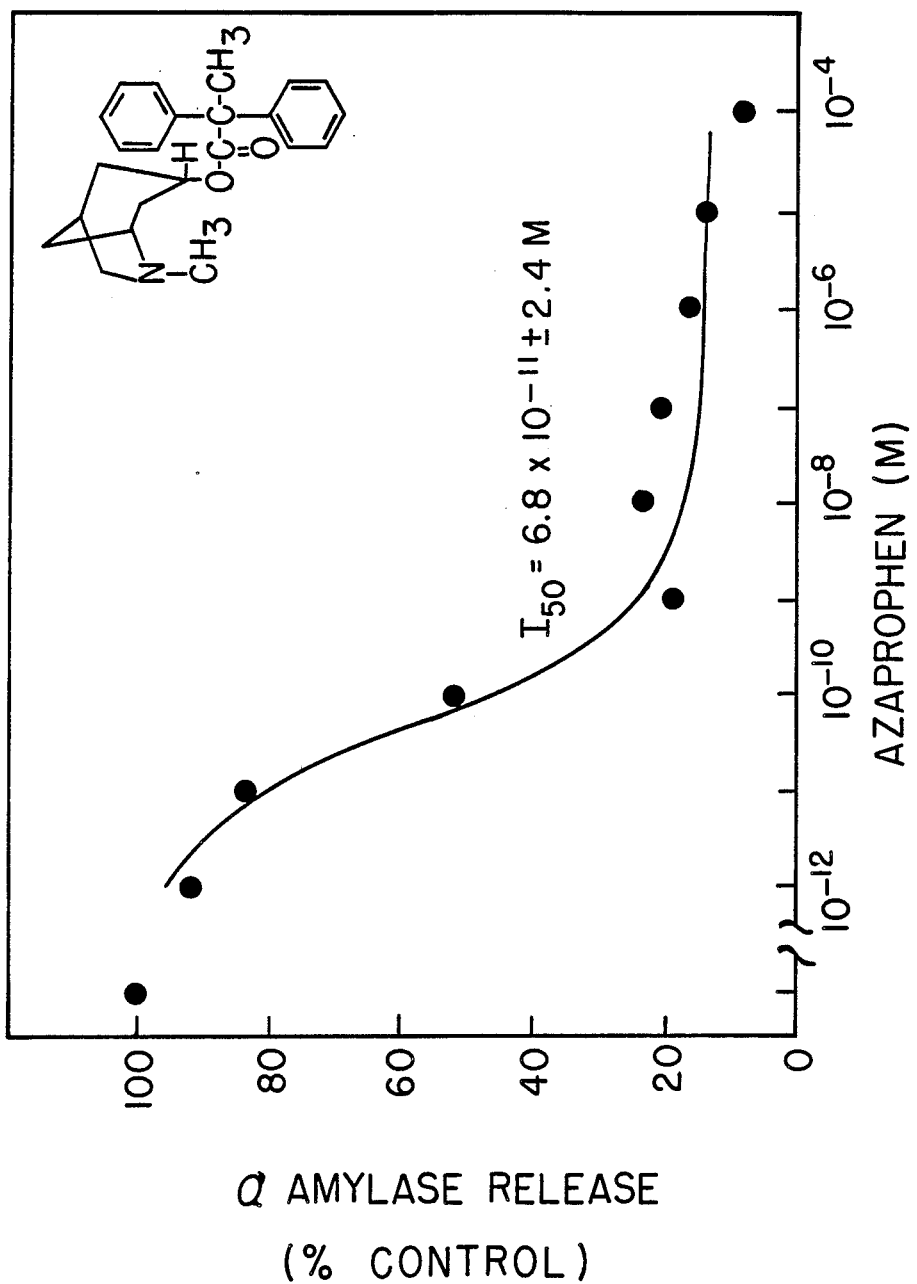
FIG. 2 illustrates the inhibition of the release of $\alpha$-amylase from pancreatic acini cells induced by $10^{-5}$M carbachol by azaprophen.

FIG. 1 shows the inhibition of the ACh-induced contraction of guinea pig ileum by azaprophen. The $pA_2$ is 10.4 ($K_B=3.9\times 10^{-11}$M), which is 50 to 2350 times more potent than aprophen, benactyzine, atropine, QNB and adiphenine as setforth in the Table. FIG. 2 shows the inhibition of the carbachol-induced release of -amylase from pancreatic acini cells. The $I_{50}$ is $6.8\times 10^{-11}$M, which is 30 to 5,000 times lower than aprophen, benactyzine and QNB, and 10 times better than atropine. A comparison of the particular potencies of azaprophen with other known antimuscarinic agents is summarized in the Table.

EXAMPLE

This working example setforth below illustrates the preparation of a representative composition, but in no way limits the scope of this invention.

6-Methyl-6-azabicyclo[3.2.1]octane-3-α-ol 2,2-diphenylpropionate Hydrochloride (Azaprophen)

Azaprophen and the benzilate ester of 6-methyl-6-azabicyclo[3.2.1]octane-3-α-ol were synthesized from 6-methyl-3-oxo-6-azabicyclo 3.2.1 octane as shown in the previously mentioned "Chemical Reaction Sequence For Preparing Azaprophen". The ketone was reduced to a mixture of isomeric alcohols with lithium aluminum hydride. The alcohol mixture was treated with 2,2-diphenylpropionyl chloride or benziloyl imidazole to give a mixture of esters. The desired products were obtained as a waxy solid which were purified as salts and were characterized by elemental and spectral analysis.

EXPERIMENTAL

6-Methyl-6-azabicyclo[3.2.1]octane-3-ols

To a suspension of 10.0 g of LiAlH$_4$ in 500 mL distilled THF was added a solution of 6-methoxy-3-oxo-6-azabicylo[3.2.1]octane (11.6 g, 0.083 mol) in 150 mL THF dropwise, and the resulting mixture was heated to reflux for 2 hours. The excess of LiAlH$_4$ was destroyed by careful addition of a 20% solution of sodium potassium tartrate, and the mixture was extracted with CH$_2$Cl$_2$. The CH$_2$Cl$_2$ solution was washed with a saturated solution of NaCl, dried (Na$_2$SO$_4$), and evaporated to give 10.0 g (85%) of 6-methyl-6-azabicyclo[3.2.1]octane-3-ols. NMR (CDCl$_3$)δ2.40 (d, 2, NCH$_2$), 2.42 (s, 3, NCH$_3$), 4.1 (m, 1, HC-OH).

The hydrogen chloride salt was prepared by adding a 3% solution of HCl (gas) in dry methanol to a solution of alcohol (250 mg) in MeOH. The analyical sample was recrystallized from MeOH/Et$_2$O to give 108 mg of pure product: mp 246°-247° C. (dec).

Anal. Calcd from C$_8$H$_{15}$NO.HCl: C, 54.08; H, 9.08; N, 7.88. Found: C, 53.94; H, 9.09; N, 7.80.

6-Methyl-6-azabicyclo[3.2.1]octane-3α-ol 2,2-Diphenylpropionate Hydrochloride (Azaprophen)

To a stirred solution of 5.5 g (0.039 mol) of isomeric 6-methyl-6-azabicyclo[3.2.1]octane-3-ols in dry THF at 0°-5° C. was added dropwise a solution of 2,2-diphenylpropionyl chloride prepared from 2,2-diphenylpropionic acid (4.64 g, 0.019 mol) and thionyl chloride. After stirring overnight at 25° C., the precipitate was separated by filtration and washed with dry THF. The residue obtained on evaporation of the solvents from the filtrate was dissolved in CH$_2$Cl$_2$ (50 mL) and washed with 5% NaHCO$_3$ solution and saturated sodium chloride solution, and dried (Na$_2$SO$_4$). The residue on evaporation was chromatographed on silica gel (200 g) using CHCl$_3$:MeOH:NH$_4$OH (80:18:2) as eluant to give 4.51 g (66%) of pure free base as a waxy solid. $^1$H NMR (CDCl$_3$)δ1.96 (s, 3, CH$_3$), 2.11 (s, 3, NCH$_3$), 5.22 (t, 1, >CHO—), 7.12-7.38 (aromatics).

The hydrogen chloride salt was prepared by treating the above free base with a solution of 3% HCl in dry MeOH. Recrystallization of the solid obtained from EtOAc/ET$_2$O gave 3.60 g (48%) of azaprophen: mp 187°-191° C. $^1$H NMR (CDCl$_3$)δ1.97 (s, 3, CH$_3$), 2.12 (d, 3, NCH$_3$), 2.47 (d, 2, NCH$_2$), 5.35 (m, 1, CHO), 7.12-7.63 (ArH).

Anal. Calcd for C$_{23}$H$_{27}$NO$_2$.HCl: C, 71.58; H, 7.31; N, 3.63. Found: C, 71.64; H, 7.32; N, 3.62.

6-Methyl-6-azabicyclo[3.2.1]octane-3α-ol Benzilate Fumarate

To a stirred solution of 423 mg (3 mmol) of 6-methyl-6-azabicyclo[3.2.1]octane-3-ols in 30 mL acetone was added 417 mg (1.5 mmol) benziloyl imidazole (prepared from benzylic acid and carbonyl diimidazole). After stirring overnight at 25° C. the residue obtained on evaporation was placed on a silica gel (100 g) column and eluted with a solvent mixture of CHCl$_3$:MeOH:NH$_4$OH (80:18:2) to give 200 mg (38%) of free base.

A solution of the free base in MeOH (1mL) was treated with fumaric acid (33 mg) in 1 mL of MeOH, diluted with ether and cooled. The fumarate salt crystals were separated by filtration, washed with ether, and dried to give 153 mg (35%) of product: mp 204°-205° C. $^1$H NMR (CDCl$_3$)δ2.61 (s, 3, NCH$_3$), 3.45 (s, 3, CH$_3$OH), 5.22 (t, 1, >CHO—), 6.58 (s, 1, —CH═CH—), 7.15-7.58 (aromatics).

Anal. Calcd for C$_{22}$H$_{25}$NO$_3$.½HOOCCH═CHCOOH, CH$_3$OH: C, 68.01; H, 7.08; N, 3.17. Found: C, 68.06; H, 7.10; N, 3.15.

UTILITY

Compositions of this invention represented by a compound such as azaprophen and pharmaceutical compositions thereof have been found to exhibit extremely potent antimuscarinic activity.

As previously disclosed herein, applicants have determined, for example, that azaprophen is 10 to 5,000 times more potent as an antimuscarinic agent than other compounds known to be used for this purpose. Additionally, utilities for these compositions include (1) antidotes for organophosphate poisoning, (2) coronary insufficiency, (3) cerebral vasospasms; (4) endarteritis, (5) spastic colitis, (6) renal and hepatic colic, (7) peptic ulcer, (8) cholecystitis, (9) dysmenorrhea, and (10) exytocic agents.

These compositions may be used as medicaments, for example, in the form of pharmaceutical preparations, which contain such compounds together with pharmaceutically acceptable, organic or inorganic, solid or liquid excipients which are suitable for systemic, for example, oral, or parenteral administration. Moreover, these preparations may, be in the solid form, for example, as tablets, dragees or capsules, or in liquid form, for example, as solutions, suspensions or emulsions. They may contain auxiliary substances, such as preservatives, stabilizers, wetting agents or emulsifiers, salts for controlling the osmotic pressure, buffers, dye stuffs or flavoring substances. The pharmaceutical preparations, which may be formulated by methods which are themselves known, may also contain other therapeutically valuable substances.

TABLE

Antimuscarinic Activity of Azaprophen and Standard Anticholinergic Compounds

| Compound | Guinea pig ileum contraction | | Pancreatic acini α-amylase release |
|---|---|---|---|
| | pA$_2$ Value | [K$_B$ (M)] | I$_{50}$ (M) |
| Azaprophen | 10.4 ± 0.4 | 3.9 × 10$^{-11}$ | 6.8 × 10$^{-11}$ ± 2.4 |
| Aprophen | 8.5 ± 0.1 | 3.1 × 10$^{-9}$ | 1.1 × 10$^{-8}$ ± 0.2 |
| Adiphenine | 7.1 ± 0.3 | 9.2 × 10$^{-8}$ | 3.5 × 10$^{-7}$ ± 0.3 |
| Benactyzine | 8.2 ± 0.8 | 6.5 × 10$^{-9}$ | 3.0 × 10$^{-8}$ ± 0.5 |
| Atropine | 8.7 ± 0.1 | 2.0 × 10$^{-9}$ | 5.9 × 10$^{-10}$ ± 5.7 |
| QNB | 8.7 ± 0.9 | 2.0 × 10$^{-9}$ | 2.1 × 10$^{-8}$ ± 0.6 |

The symbols pA$_2$ represent the antagonistic activity and the symbols QNB represent quinuclidinyl benzylate.

We claim:

1. An azabicycloalkane phenyl substituted alkane carboxylate compound having the formula

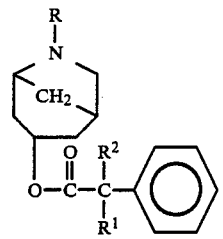

wherein R represents lower alkyl groups having 1 to 7 carbon atoms; R$^1$ represents hydrogen, phenyl, cyclohexyl, and cyclopentyl; and R$^2$ represents lower alkyl groups having 1 to 7 carbons, hydroxymethyl, and hydroxyl; and pharmaceutically acceptable acid addition salts thereof.

2. The compound of claim 1 wherein R is selected from the group consisting of methyl, ethyl and propyl.

3. The compound of claim 2 wherein R and R$^2$ are methyl and R$^1$ is phenyl.

4. The compound of claim 2 wherein R and R$^2$ are ethyl and R$^1$ is phenyl.

5. The compound of claim 2 wherein R is methyl and R$^2$ is ethyl and R$^1$ is phenyl.

6. The compound of claim 2 wherein R is ethyl and R$^2$ is methyl and R$^1$ is phenyl.

7. A method for the treatment or prophylaxis of nerve gas poisoning comprising administering, to an animal, an anticholinergic amount of a compound of claim 1.

8. The method of claim 7 wherein the administration is effected prior to poisoning.

9. The method of claim 7 wherein the administration is effected subsequent to poisoning.

10. The method of claim 7 wherein R and R$^2$ are selected from the group consisting of methyl, ethyl and propyl.

11. The method of claim 10 wherein R and R$^2$ are methyl.

* * * * *